United States Patent
Barak

(10) Patent No.: US 8,399,823 B2
(45) Date of Patent: Mar. 19, 2013

(54) SYRINGE MOVEMENT MECHANISM AND CONTROL SYSTEM THEREFOR

(76) Inventor: Swi Barak, Caesarea (IL)

(*) Notice: Subject to any disclaimer, the term of this patent is extended or adjusted under 35 U.S.C. 154(b) by 457 days.

(21) Appl. No.: 12/707,803

(22) Filed: Feb. 18, 2010

(65) Prior Publication Data

US 2010/0145263 A1 Jun. 10, 2010

Related U.S. Application Data

(63) Continuation-in-part of application No. 11/615,913, filed on Dec. 22, 2006, now Pat. No. 7,766,492.

(51) Int. Cl.
*H01J 40/14* (2006.01)
(52) U.S. Cl. ........................... 250/221; 250/239
(58) Field of Classification Search ............ 250/221, 250/239, 231.13; 604/67, 118, 121, 152; 600/300, 407, 427
See application file for complete search history.

(56) References Cited

U.S. PATENT DOCUMENTS

| 5,034,004 | A | | 7/1991 | Crankshaw |
| 5,232,449 | A | | 8/1993 | Stern |
| 5,254,096 | A | * | 10/1993 | Rondelet et al. .............. 604/152 |
| 2009/0005730 | A1 | | 1/2009 | Gerlach |

FOREIGN PATENT DOCUMENTS

| EP | 0402553 | 11/1989 |
| EP | 1329232 | 1/2003 |

* cited by examiner

*Primary Examiner* — Que T Le

(57) ABSTRACT

A movement and control mechanism for operating a syringe is disclosed. The movement mechanism includes a rotatable shaft and two rods disposed coaxially to the shaft and a plunger associated unit. The plunger unit accommodates a plunger of a syringe and axially translates upon rotation of the shaft. An electrical sensor system is implemented with the movement mechanism for detecting the presence of a syringe plunger in the plunger associated unit during the operation of the mechanism. The electrical sensor system forms an interruptible electrical circuit between the rods of the movement mechanism, allowing continuous detection of the presence of a plunger in the plunger associated unit during axial translation of the plunger associated unit along the rods.

14 Claims, 4 Drawing Sheets

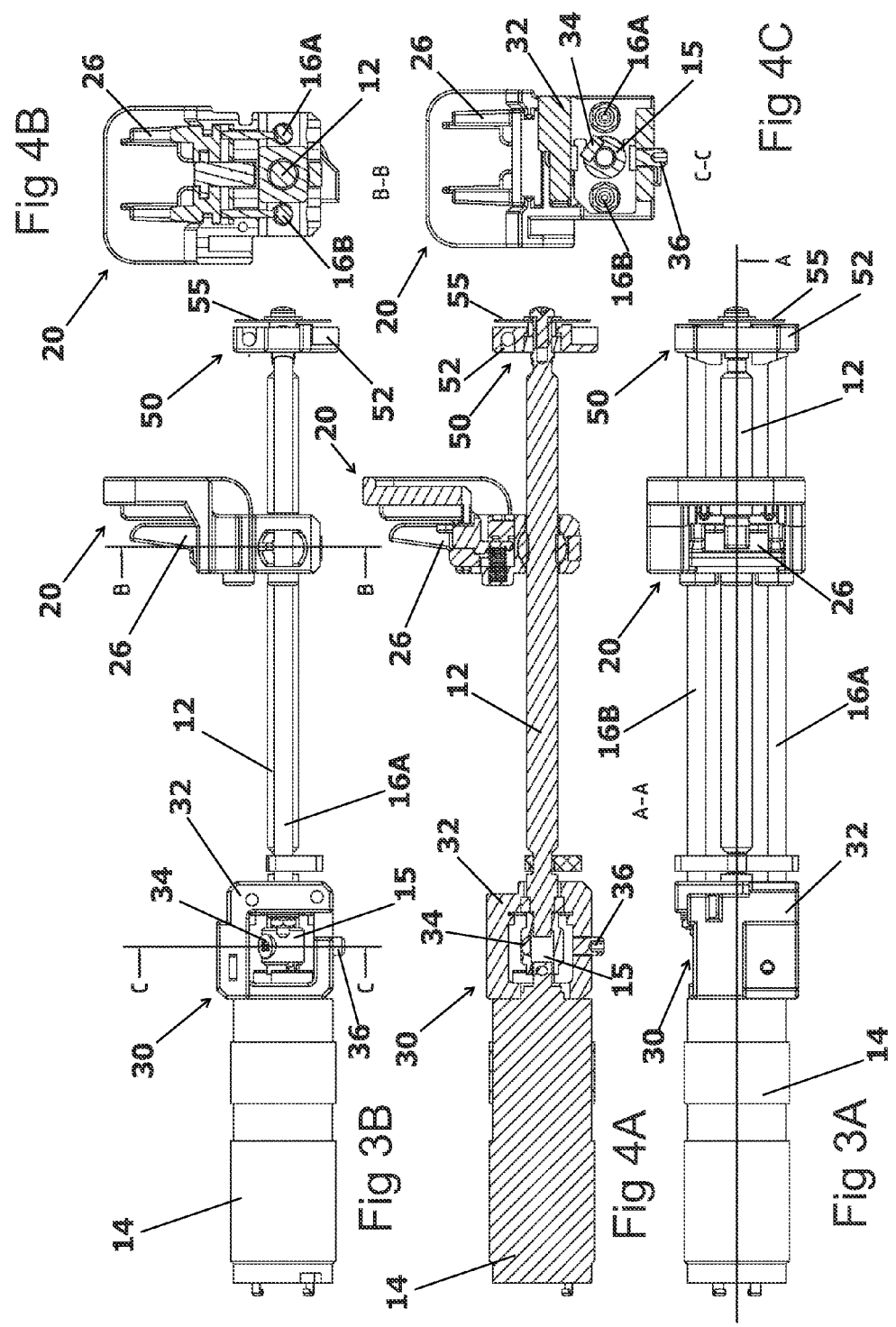

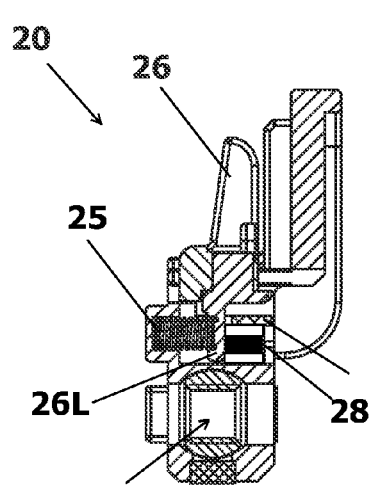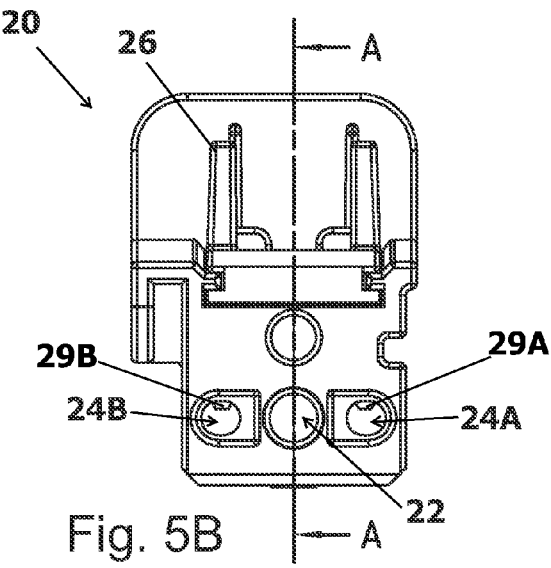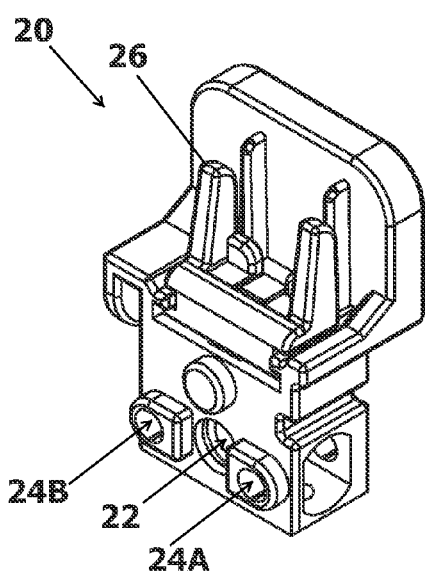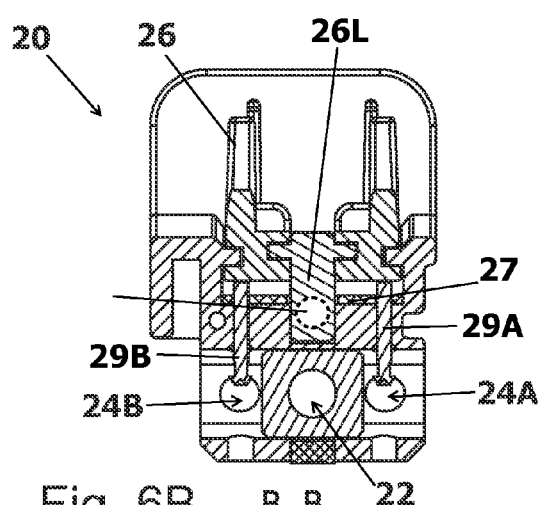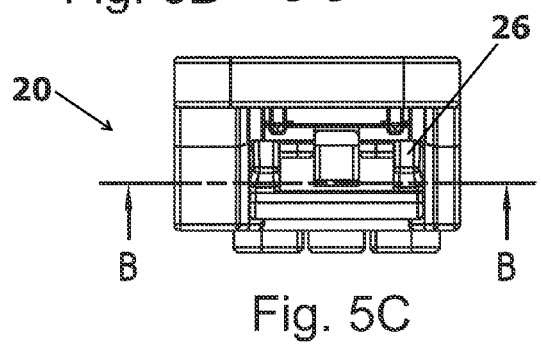
Fig. 6A
Fig. 5B
Fig. 6B
Fig. 5A
Fig. 5C

SYRINGE MOVEMENT MECHANISM AND CONTROL SYSTEM THEREFOR

CROSS-REFERENCE TO RELATED APPLICATIONS

The present application is a continuation-in-part of U.S. patent application Ser. No. 11/615,913, filed Dec. 22, 2006 now U.S. Pat. No. 7,766,492, entitled "SYRINGE PUMP." The present application claims the benefit of domestic priority to the aforesaid application and incorporates the content thereof herein by reference.

TECHNICAL FIELD

The present invention generally relates to medical devices. In particular, the invention relates to improvements to the movement and control mechanisms of a syringe pump.

BACKGROUND ART

It is believed that the current state-of-the-art is represented by US patent application Ser. No. 2009/0005730; U.S. Pat. Nos. 5,232,449 and 5,034,004; European patent application Ser. No. 0402553; European patent Ser. No. 1329232 and international patent application Ser. No. PCT/US0000/029657.

SUMMARY OF THE INVENTION

In accordance with one aspect of the present invention a movement and control mechanism for operating a syringe is provided. The movement mechanism comprises a rotatable shaft, at least one rod disposed coaxially to the shaft and a plunger associated unit, accommodating the plunger of the syringe and axially translated upon the rotation of the shaft.

In accordance with another aspect of the present invention an electrical sensor system implemented with the movement mechanism for detecting the plunger of the syringe, during the operation of the mechanism, is further provided.

In accordance with yet another aspect of the present invention a control system for the movement mechanism, controlling the operation the thereof, is still further provided.

BRIEF DESCRIPTION OF THE DRAWINGS

The present invention will be understood and appreciated more fully from the following detailed description taken in conjunction with the appended drawings in which:

FIG. 3A is a top view of the movement and control mechanism shown in FIGS. 1A and 1B;

FIG. 3B is a side view of the movement and control mechanism shown in FIGS. 1A and 1B;

FIG. 4A is a cross-sectional view of section A-A of the movement and control mechanism shown in FIG. 3A;

FIG. 4B is a cross-sectional view of section B-B of the plunger associated unit of the movement and control mechanism shown in FIG. 3B;

FIG. 4C is a cross-sectional view of section C-C of the magnetic revolution sensor assembly of the movement and control mechanism shown in FIG. 3B;

FIG. 5A is an isometric view of the of the plunger associated unit of the movement and control mechanism;

FIG. 5B is a front view of the of the plunger associated unit of the movement and control mechanism;

FIG. 5C is a top view of the of the plunger associated unit of the movement and control mechanism;

FIG. 6A is a cross-sectional view of section A-A of the plunger associated unit shown in FIG. 5B;

FIG. 6B is a cross-sectional view of section B-B of the plunger associated unit shown in FIG. 5C;

Figure 1:
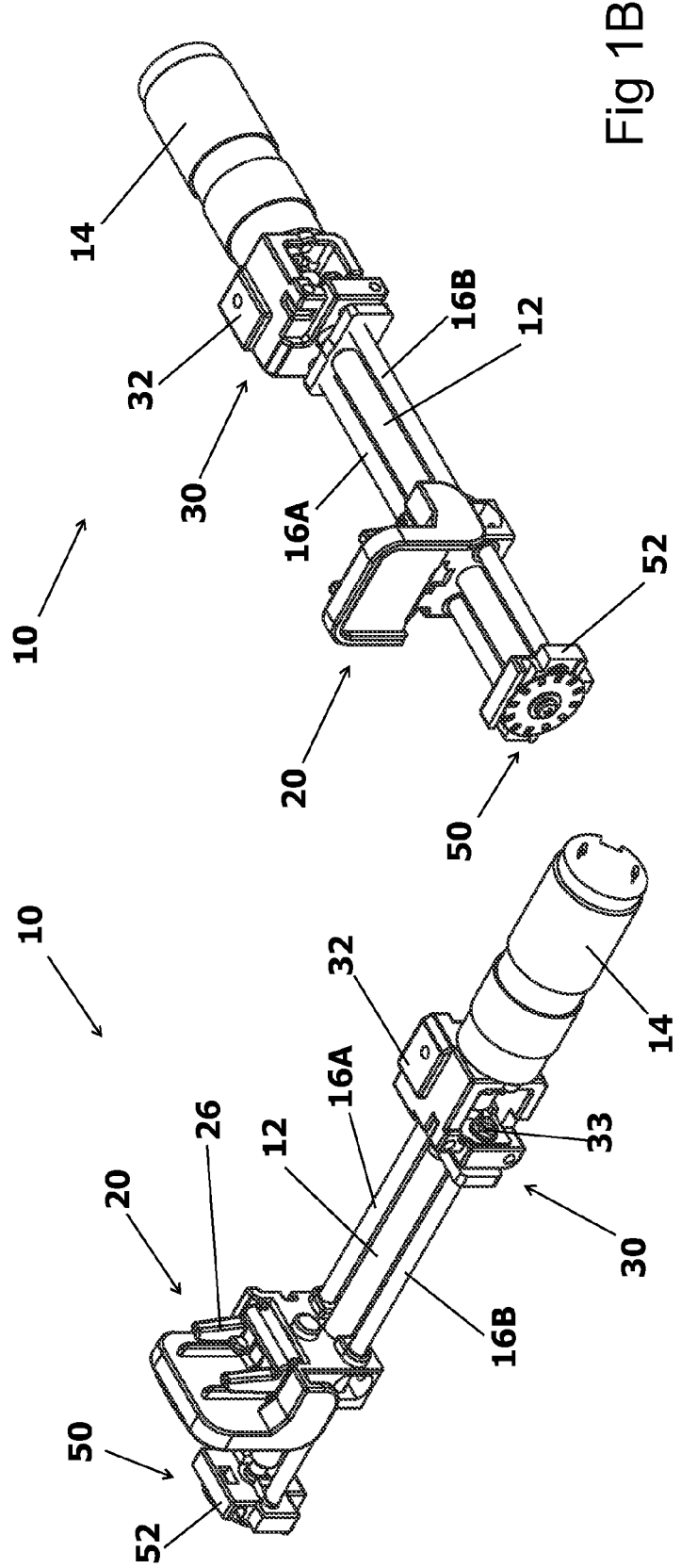
FIGS. 1A and 1B are isometric views of the movement and control mechanism of the invention.

While the invention is susceptible to various modifications and alternative forms, specific embodiments thereof have been shown by way of example in the drawings. The components in the drawings are not necessarily to scale, emphasis instead being placed upon clearly illustrating the principles of the present invention.

DISCLOSURE OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

The Syringe Operating Movement Mechanism of the Invention

Figure 2:
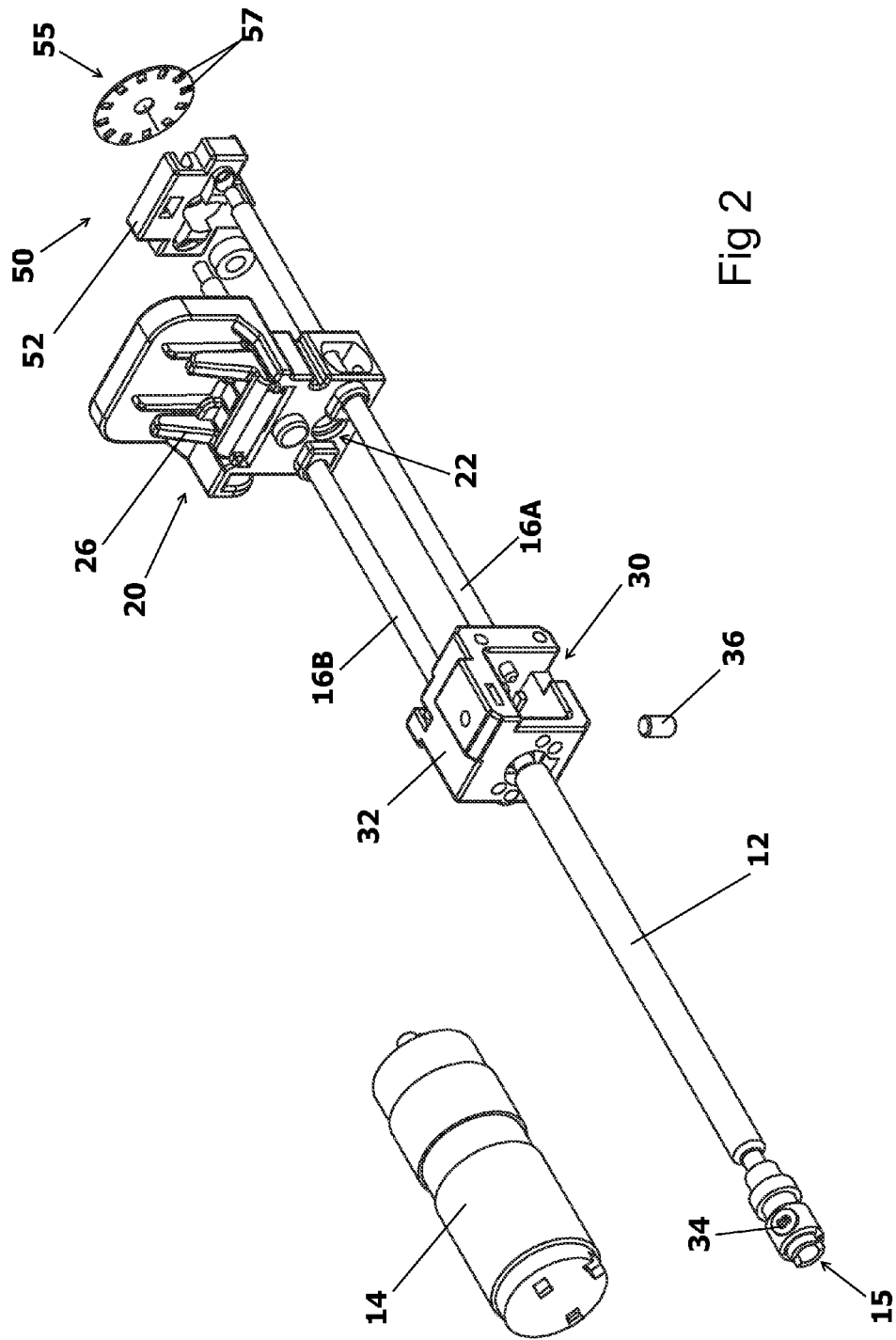
FIG. 2 is an exploded view of the movement and control mechanism shown in FIGS. 1A and 1B.

In accordance with some embodiments of the present invention, reference is now made to FIGS. 1A to 4C, showing movement and control mechanism 10. Movement and control mechanism (hereinafter MCM) 10 can be implemented in a variety of syringe pumps or any other devices activating syringes; hence it should be acknowledged that the implementation with a syringe pump is merely exemplar and thus MCM 10 can be beneficially implemented in any device or appliance operating a syringe. MCM 10 comprises shaft 12 rotationally coupled to motor 14 via coupler 15 and rods 16A and 16B extending coaxially to shaft 12. Motor 14 is preferably characterized by the ability of performing up to 7000 revolutions per minute (RPM) and producing a rotational torque of between 5 to 15 mN/m (milli-Newton per meter) and preferably of ~10 mN/m. It is noted that the average operational rotational speed of motor 14 is preferably 3500 RPM. Motor 14 is typically coupled to a planetary gear mechanism, which is preferably incorporated within the housing of motor 14; the planetary gear reduces the rotational output speed of motor 14 and enhancing the rotational output torque at the ratio of about 1/22.

Shaft 12 is furnished with a screw threading (not shown). Plunger associated unit (hereinafter PAU) 20 is disposed on shaft 12 and rods 16A and 16B. Shaft 12 and rods 16A and 16B extend through PAU 20 via apertures therein. Central aperture 22, accommodating shaft 12, comprises a respectively matching screw threading, whereas flanking apertures 24A and 24B, accommodating rods 16A and 16B, furnished with a relatively smooth surface for facilitating a contiguous sliding of the latter therealong.

Rods 16A and 16B prevent a rotational movement of PAU 20; thereby upon rotation of shaft 12, PAU 20 is axially translated along rods 16A and 16B. The velocity of the axial translation is a function of the rotary speed conferred to shaft 12 by motor 14 and the parameters of the helical pitch of the screw threading furnishing shaft 12 and central aperture 22 at PAU 20. The preferred parameters of the helical pitch of the screw threading furnishing shaft 12 and central aperture 22 at PAU 20 are from about 0.5 to about 1.5 mm/revolution and preferably ~0.8 mm/revolution.

PAU 20 comprises plunger fastener 26. PAU 20 and fastener 26 form a part of an electrical sensor system detecting the presence of a plunger therebetween. The structural and functional features of PAU 20 and the electrical sensor system will be explained in some details infra.

Control System and Method for the Movement Mechanism

MCM 10 comprises a magnetic revolution sensor assembly 30 and optical encoder system 50, for the control of the operation of MCM 10. Magnetic revolution sensor assembly (hereinafter MRSA) 30 comprises MRSA housing 32, coupler 15, magnetic or ferromagnetic element 34, magnetically conductive barrel 36 and a reed-switch (not shown). In MRSA housing 32 the proximal ends of rods 16A and 16B are anchored. The proximal ends of rods 16A and 16B are typically furnished with a screw threading and tightened by the means of nuts 33 to MRSA housing 32. Shaft 12 passes throughout MRSA housing 32 and the proximal end thereof is furnished with coupler 15.

Coupler 15 couples the rotational movement of motor 14 with the rotation of shaft 12. Coupler 15 comprises magnetic or ferromagnetic element 34, disposed offset the longitudinal centerline axis of shaft 12, as a cam on coupler 15. Magnetically conductive barrel 36 is accommodated at the bottom portion of MRSA housing 32. Magnetically conductive barrel 36 is characterized by the ability of efficiently conducting the magnetic field formed by element 34, so that upon positioning of the latter in the vicinity of the former, i.e. vis-á-vis each other while element 34 is oriented towards the bottom portion of MRSA housing 32, the reed-switch, disposed underneath conductive barrel 36 is activated.

Encoder system 50 comprises terminal encoder block 52, in which the distal ends of rods 16A and 16B are anchored. The distal ends of rods 16A and 16B are typically furnished with a screw threading and tightened by the means of nuts (not shown) to terminal encoder block 52. Shaft 12 passes throughout block 52 and terminates with perforated disc 55, rotationally coupled to shaft 12. Encoder system 50 comprises at least one infrared LED (light emitting diode) or other source of infrared radiation (not shown) and at least two infrared sensors (not shown). At least the infrared LED or the infrared sensors can be mounted onto terminal encoder block 52. The infrared LED disposed vis-á-vis the infrared sensors in such a manner that perforated disc 55 is located in-between, so that perforations 57 therein can form a continuous optical path from the former to the latter, whereas the non-perforated portions of disc 55 obstruct the aforementioned path. The infrared sensors are positioned adjacently to each other so that both of them can be illuminated by the infrared LED via a single perforation 57. Perforated disc 55 comprises 12 perforations 57; whereby 48 discrete events are detected encoder system 50 upon a complete rational cycle of disc 55. An event as referred to herein constitutes a commencement or termination of the illumination by the infrared LED onto either of the infrared sensors. The adjacent positioning of the infrared sensors so that both of them can be illuminated by the infrared LED via a single perforation 57 provides for identifying the direction of the rotation of disc 55, i.e. a rotation in a clockwise or counterclockwise direction.

A control module (not shown) performs a correlation between the counts of encoder system 50 and MRSA 30; whereby verification of the correctness of the readings and the absence of malfunction of either encoder system 50 or MRSA 30 is achieved. The correlation between the counts of encoder system 50 and MRSA 30 is preferably performed in the following manner. Per complete rotational cycle of shaft 12 MRSA 30 detects two events, namely turning-on events and turning-off events of the reed-switch; whereas encoder system 50 detects 48 events, namely a commencement or termination of the illumination onto either of the infrared sensors. However a given event detected by MRSA 30 do not always precisely correspond or occur concurrently with a particular event detected encoder system 50; since the reed-switch that is activated by the magnetic field induced by magnetic element 34 and conveyed by conductive barrel 36 is not always turned-on and turned-off at precisely the same angular position of element 34. Consequently the activation of the reed-switch of MRSA 30 may precede or exceed a particular event detected encoder system 50. In light of the foregoing, the algorithm of the method for controlling the operation of MCM 10 counts the events detected by MRSA 30 and events detected by encoder system 50 and compares the former to the latter in an accumulative manner. For instance if at a first rotational cycle of shaft 12 turning-on event of the reed-switch of MRSA 30 is detected concurrently with the occurrence of event N detected encoder system 50, at the second rotational cycle of shaft 12 the very same turning-on event of the reed-switch of MRSA 30 may be detected with delta of 1 in respect to the aforesaid event N detected encoder system 50, namely concurrently with the occurrence of event N+1 or N−1 detected encoder system 50. The value of the threshold for the aforementioned delta, used for triggering an alarm or halting the operation MCM 10, is preferably set on 2 or 3. The aforementioned accumulative comparative count of the events detected by MRSA 30 versus the events detected by encoder system 50 provides for eliminating a methodic error in operation of MCM 10; thus if the count of a single event is missed during each rotational cycle, the alarm shall be triggered or the operation of MCM 10 shall be halted after the completion of 2 or 3 rotational cycles.

Plunger Presence Detection Electrical Sensor System

In accordance with some embodiments of the present invention, reference is now made to FIGS. 5A to 6B, showing PAU 20 and the electrical sensor system for the detection of the presence of a syringe's plunger therein. PAU 20 comprises plunger fastener 26. PAU 20 and fastener 26 form a part of an electrical sensor system detecting the presence of a plunger therebetween. Fastener 26 is biased by spring 25 towards PAU 20. Fastener 26 comprises downwardly facing lever 26L.

PAU 20 comprises PCB plate 27 in the centre of which knob cutoff switch 28 is mounted. The knob of cutoff switch 28 extends up to lever 26L of fastener 26. Upon introduction of the thumb-rest plate of the plunger of a syringe (not shown) in-between PAU 20 and fastener 26, lever 26L is translated away from PCB plate 27 and the button of cutoff switch 28 is released. Alternatively upon removal of the thumb-rest plate of the plunger of a syringe (not shown) from PAU 20, lever 26L biased by spring 25 is translated towards PCB plate 27 and the button of cutoff switch 28 is pushed.

PCB plate 27 further comprises probes 29A and 29B. Examples of probes 29A and 29B include biased gilded probes of 100-05 Series, catalogue code—100 (2.54) Centers/050 (1.27) Stroke, available form QA Technology Company, Inc. at 110 Towle Farm Road, Hampton, N.H. 03842 USA. Probes 29A and 29B are mounted on the flanks of PCB plate 27 and each probe is electrically connected to a respective terminal of cutoff switch 28 mounted in-between at the centre of PCB plate 27. Probes 29A and 29B extend throughout PAU 20 and slightly protrude into flanking apertures 24A and 24B. Probes 29A and 29B form dynamic electrical contact with electrically conductive rods 16A and 16B, during the contiguous sliding of the former along the cylindrical surface of the latter. Rods 16A and 16B serve the purpose of two respective electrical conduits. Electrically conductive wires (not shown) are connected to rods 16A and 16B, for by being instance tightened by the means of nuts 33 to the proximal ends thereof.

An interruptible electrical circuit of the sensor system for the detection of the presence of a syringe's plunger in-between PAU 20 and fastener 26 is connected to the control module (not shown) of MCM 10. The interruptible electrical circuit of the sensor system for the detection of the presence of a syringe's plunger comprises the aforementioned electrically conductive wires, rods 16A and 16B, probes 29A and 29B, PCB plate 27 and cutoff switch 28. Cutoff switch 28, acts as the interrupting means of the electrical circuit of the sensor system for the detection of the presence of a syringe's plunger; whereas lever 26L of fastener 26 acts as the mechanical means for actuating cutoff switch 28.

Provided that there is no a thumb-rest plate of the plunger of a syringe (not shown) in-between PAU 20 and fastener 26, lever 26L is pushing onto cutoff switch 28 and thereby interrupting the continuity of the electrical circuit of the sensor system for the detection of the presence of a syringe's plunger. However upon introduction of the thumb-rest plate of the plunger of a syringe (not shown) in-between PAU 20 and fastener 26, lever 26L is translated away from PCB plate 27 and the button of cutoff switch 28 is released; whereby the continuity of the electrical circuit of the sensor system for the detection of the presence of a syringe's plunger is formed and thus the aforementioned presence is detected. It is noted that the continuity of the electrical circuit of the sensor system for the detection of the presence of a syringe's plunger is remained during the translation of PAU 20 due to the dynamic electrical contact between probes 29A and 29B and the surface of electrically conductive rods 16A and 16B, formed inter alia during the contiguous sliding of the former along the cylindrical surface of the latter.

It will be appreciated by persons skilled in the art that the present invention is not limited by what has been particularly shown and described herein above. Rather the scope of the invention is defined by the claims which follow:

The invention claimed is:

1. An electrical sensor system implemented with a movement mechanism for operating a syringe, said system detects the presence of a plunger of said syringe, said system comprising:
   [a] at least two parallel disposed rods, said parallel disposed rods and are characterized by at least electrically conductive surface, and
   [b] a plunger associated unit, accommodating said plunger of said syringe, said plunger associated unit comprising at least:
      [1] a fastener, accommodating a thumb-rest plate of said plunger;
      [2] at least two flanking apertures and, respectively accommodating said at least two parallel disposed rods;
      [3] a pushably activated cutoff switch, said cutoff switch is activated/deactivated by said fastener;
      [4] at least two probes, said probes are electrically coupled to the respective electric terminals of said cutoff switch;
   wherein said plunger associated unit is slidably translatable along said at least two parallel disposed rods;
   wherein said at least two probes dynamically form an electrical contact with said electrically conductive surface of said rods, wherein said contact is maintained during a contiguous sliding of the former along said electrically conductive surface of the latter;
   wherein upon introduction of said thumb-rest plate of said plunger in-between said plunger associated unit and said fastener, said cutoff switch is activated/deactivated; whereas upon removal of said thumb-rest plate of said plunger, said cutoff switch is respectively deactivated/activated;
   wherein an interruptible electrical circuit is formed between said rods, whereby allowing continuously detecting the presence of said plunger in said plunger associated unit during said slidable translation of the latter along said electrically conductive surface of the former.

2. The electrical sensor system as in claim 1, wherein said fastener is biased by spring towards said plunger associated unit acts as a physical means affecting said cutoff switch.

3. The electrical sensor system as in claim 1, wherein said presence is a correct positioning of said thumb-rest plate of said plunger in-between said fastener and said plunger associated unit.

4. The electrical sensor system as in claim 1, wherein the absence of said presence is at least one selected form the group consisting of: an incorrect positioning, malposition or absence of said thumb-rest plate of said plunger in-between said fastener and said plunger associated unit.

5. The electrical sensor system as in claim 1, wherein said fastener comprising a downwardly facing lever.

6. The electrical sensor system as in claim 1, wherein said cutoff switch is a pushable knob.

7. The electrical sensor system as in claim 1, wherein said plunger associated unit further comprising a PCB plate, onto which said cutoff switch and said probes are mounted.

8. The electrical sensor system as in claim 1, wherein said probes are biased probes.

9. In combination, the electrical sensor system of claim 1 and a movement and control mechanism for operating a syringe, said mechanism comprising:
   [a] a rotatable shaft, said shaft is furnished with a screw threading;
   [b] a motor rotationally coupled to said shaft;
   [c] at least one rod disposed coaxially to said shaft, and
   [d] a plunger associated unit, accommodating a plunger of a syringe, said plunger associated unit comprising at least:
      [1] a fastener, accommodating a thumb-rest plate of said plunger;
      [2] a central aperture, said central aperture is furnished with a respectively matching screw threading, and
      [3] at least one flanking aperture, said at least one flanking aperture is furnished with a relatively smooth surface for facilitating a contiguous slidable translation therealong;
   wherein said rotatable shaft is accommodated within said central aperture, thereby the screw threading of the former is operationally interlocking with the respectively matching screw threading of the latter;
   wherein said at least one rod is accommodated within said at least one flanking aperture;
   whereby upon rotation of said motor, an axial translation of said plunger associated unit along said rotatable shaft is achieved.

10. The combination as in claim 9, further comprising a coupler, said coupler coupling the rotation of said motor with the rotation of said shaft.

11. The combination as in claim 9, wherein said at least one rod are said at least two rods disposed parallel to said shaft and wherein said at least one flanking aperture comprises two flanking apertures, respectively accommodating said two rods.

12. The combination as in claim 9, wherein said motor is characterized by an operational rotational speed of about 160 RPM and rotational torque of about 220 mN/m.

13. The combination as in claim 9, wherein said motor is furnished with a planetary gear.

14. The combination as in claim 9, wherein said screw threading is characterized by a helical pitch of about 0.8 mm per revolution.

* * * * *

UNITED STATES PATENT AND TRADEMARK OFFICE
CERTIFICATE OF CORRECTION

PATENT NO. : 8,399,823 B2
APPLICATION NO. : 12/707803
DATED : March 19, 2013
INVENTOR(S) : Swi Barak Page 1 of 1

It is certified that error appears in the above-identified patent and that said Letters Patent is hereby corrected as shown below:

On the Title Page

Item (63) Related U.S. Application Data:
Replace "application No. 11/615,913" with --application No. 11/615,931--.

Signed and Sealed this
Sixth Day of October, 2020

Andrei Iancu
*Director of the United States Patent and Trademark Office*